United States Patent [19]

Andersson et al.

[11] Patent Number: 5,331,953
[45] Date of Patent: Jul. 26, 1994

[54] DEVICE IN CONNECTION WITH AN INHALER

[75] Inventors: Jan A. R. Andersson, S. Sandby; Nils G. Nilsson, Lund; Per-Olof S. Fagerström, Bjärred; Thomas M. Wendel, Genarp, all of Sweden

[73] Assignee: Aktiebolaget Draco, Sweden

[21] Appl. No.: 88,628

[22] PCT Filed: Mar. 2, 1990

[86] PCT No.: PCT/SE90/00137
§ 371 Date: Jan. 7, 1991
§ 102(e) Date: Jan. 7, 1991

[87] PCT Pub. No.: WO90/10470
PCT Pub. Date: Sep. 20, 1990

Related U.S. Application Data

[63] Continuation of Ser. No. 603,686, Jan. 7, 1991.

[30] Foreign Application Priority Data

Mar. 7, 1989 [SE] Sweden .................. 8900793-4

[51] Int. Cl.⁵ ............................................ A61M 11/00
[52] U.S. Cl. .................... 128/200.14; 128/200.23; 128/203.15
[58] Field of Search .............. 128/200.14, 203.15, 128/203.21, 200.23, 721, 724, 204.26, 204.23, 205.23

[56] References Cited

U.S. PATENT DOCUMENTS

| | | | |
|---|---|---|---|
| 2,587,215 | 2/1952 | Priestly | 128/203.15 |
| 3,807,400 | 4/1974 | Cocozza | 128/203.15 |
| 4,109,656 | 8/1978 | Goethel et al. | |
| 4,291,688 | 9/1981 | Kistler | 128/200.14 |
| 4,484,577 | 11/1984 | Sackner et al. | 128/200.23 |
| 4,677,975 | 7/1987 | Edgar et al. | 128/200.14 |
| 4,817,822 | 4/1989 | Rand et al. | 128/200.14 |
| 4,830,022 | 5/1989 | Harshe et al. | 128/724 |
| 4,984,158 | 1/1991 | Hillsman | 128/725 |
| 5,020,527 | 6/1991 | Dessertine | 128/200.14 |
| 5,035,237 | 7/1991 | Newell et al. | 128/203.21 |
| 5,042,467 | 8/1991 | Foley | 128/200.14 |

Primary Examiner—Edgar S. Burr
Assistant Examiner—Aaron J. Lewis
Attorney, Agent, or Firm—White & Case

[57] ABSTRACT

The present invention refers to a device in connection with an inhaler intended for measuring and recording the course of inhalation of a patient. The device is intended for use in medication, e.g. clinical tests, where there is a need of afterwards being able to control if the patient has taken medicine in a prescribed way. The device comprises an electronic unit provided in the inhaler for recording of the time for each dosage of the medicine of the inhaler. A detector (16,32,36) is provided in the inhaler in connection with a passage for the airflow of inhalation, whereby the detector detects the airflow of the inhalation through the inhaler as well as the availability of the medicine at the inhalation within said passage, so that a combination of these two detected values decides if and how the performed inhalation should be recorded in the electronical unit (11,33,35).

11 Claims, 7 Drawing Sheets

DEVICE IN CONNECTION WITH AN INHALER

This application is a continuation of application Ser. No. 07/603,686, filed on Jan. 7, 1991.

FIELD OF THE INVENTION

The present invention relates to a device in connection with an inhaler intended for measuring and recording of the inhalation course of a patient. The device is intended for use in medical treatment, e.g. in clinical tests, where there is a need for recording a course of events afterwards in order to be able to verify if the patient has taken medicine in the prescribed way. The device can also be used to detect the level of trouble of the patient between the patient's visits to a doctor.

BACKGROUND OF THE INVENTION

The omission of a patient to keep up to a medication prescribed by a doctor might be the reason for an unsuccessful treatment e.g. for cronical deseases. With a desease as e.g. asthma, where a continous medication program is necessary, it is especially important that the medication is performed in a prescribed way. Investigations have proven that between 30 and 50% of the patients take medicines irregularly and incorrect when they take the medicines themselves, which fact often is not discovered by the doctor in charge. The difficulty of recording how well the patient follows the prescriptions for the medication results in an unsatisfactory security in the evaluation of clinical tests.

One type of control systems for the medication of patients, used today, the so called MEMS ® system, comprises different types of ordinary standard medicines containers, which are provided with microprocessors, which record date and moment for each opening and closing of the containers.

Another known control system, called Nebulizer Chronolog ®, consists of a small portable device, in which is contained a standard aerosol container. At each release of an aerosol dose, a contact device is actuated, whereby an electronical memory unit stores date and moment for each dosage fed out.

For a patient inhaling his medicine to receive an acceptable dosage to the lungs, however, it is necessary that the release of an aerosol dosage is coordinated with the inhalation of the patient. When using a powder inhaler device, the inhalation flow must reach a "critical flow" to make the powder dose follow the airflow and for the formation of a favourable particle picture, which can reach far enough down into the lungs.

The above disclosed known systems used today record the moment for each event when a medicine package is opened or each time a medicine dose is released, but these known systems lack the possibility of detecting if and when a satisfactory medication has been performed of the patient. With these systems one has not been able to receive a confirmation of that the patient really takes his dose and that the patient takes his dose in the prescribed way in order to get a medical effect.

Basic concept of the invention

The object of the present invention is to solve the above problems by a device in connection with an inhaler, which can measure and record if and when a satisfactory medication has been performed in a patient.

A device of the kind discussed in the beginning is according to the invention characterized in that a detector is provided in the inhaler in connection with a passage for the inhalation air-flow, whereby the detector is arranged to detect the inhalation airflow through the inhaler as well as the accessibility of the medicine at the inhalation, whereby the combination of the detected values determines if and when the inhalation should be recorded in the electronical unit.

Further advantageous features of the invention will be evident from the following description of embodiments and the sub-claims.

A change of sound or pressure occurring at the feeding of a powder dose, at the release of a pressure aerosol or at the punctuation of a powder capsule can be detected by a detector and the generated signal can subsequently be treated and recorded by the components in an electronical unit. A characteristic back noice or a pressure drop, which occurs in the inhaler at inhalation can be detected by the detector and can thereafter be treated and recorded by the electronical unit.

In order to obtain a satisfactory picture of how a patient has performed a planned medication with the aid of an inhaler, it is thus important to be able to detect the patient's own inhalation in combination with a detection of the availability of the medicine dose for the patient. In certain cases it is also important to be able to read how the course of the inhalation looks, that is how strong and how long it is, in order to be able thereby to determine if the inhalation of the patient has enough strength and duration for the obtaining of a correct deposition of active substance in the lungs.

The device according to the invention is also suitable for use in measuring and recording the level of severity of a patient's sickness state in periods between the patient's visits to a doctor. By the recording of different inhalation parameters, which correlates to the severity of the asthma desease, with the aid of the device according to the invention, the doctor can get a good picture of the development of the patient's desease during the time between the medical examinations.

The detector can be comprised of a sound detector, e.g. a microphone of the type electret microphone, but also other types of detectors, such as for example a pressure transmitter, are feasible within the scope of the invention.

SHORT DESCRIPTION OF ACCOMPANYING DRAWINGS

One embodiment of the device according to the present invention and modifications thereof are described more in detail below with reference to the accompanying drawings, wherein FIG. 1 shows an exploded view of a powder inhaler wherein the airflow through the inhaler is marked with arrows, FIG. 2 shows a cross-sectional view through a powder inhaler according to FIG. 1 with a device for measuring and recording sound according to the invention, FIGS. 3a and 3b show two alternative block diagrams of comprised electronical components in FIG. 2, FIG. 4 shows a diagram of how the microphone in FIG. 2 catches outside, disturbing noise, FIG. 5 shows a diagram of how the microphone in FIG. 2 catches inhalation noise through the inhaler, FIG. 6 shows a diagram of the measuring signal of the inhalation after passage through filter and amplifier, FIG. 7 shows a cross sectional view through a dose aerosol with a device according to the invention, and FIG. 8 shows a cross sectional view through a powder inhaler for gelatine capsules with a device according to the invention.

DETAILED DESCRIPTION OF PREFERRED EMBODIMENTS OF THE INVENTION

Figure 1:
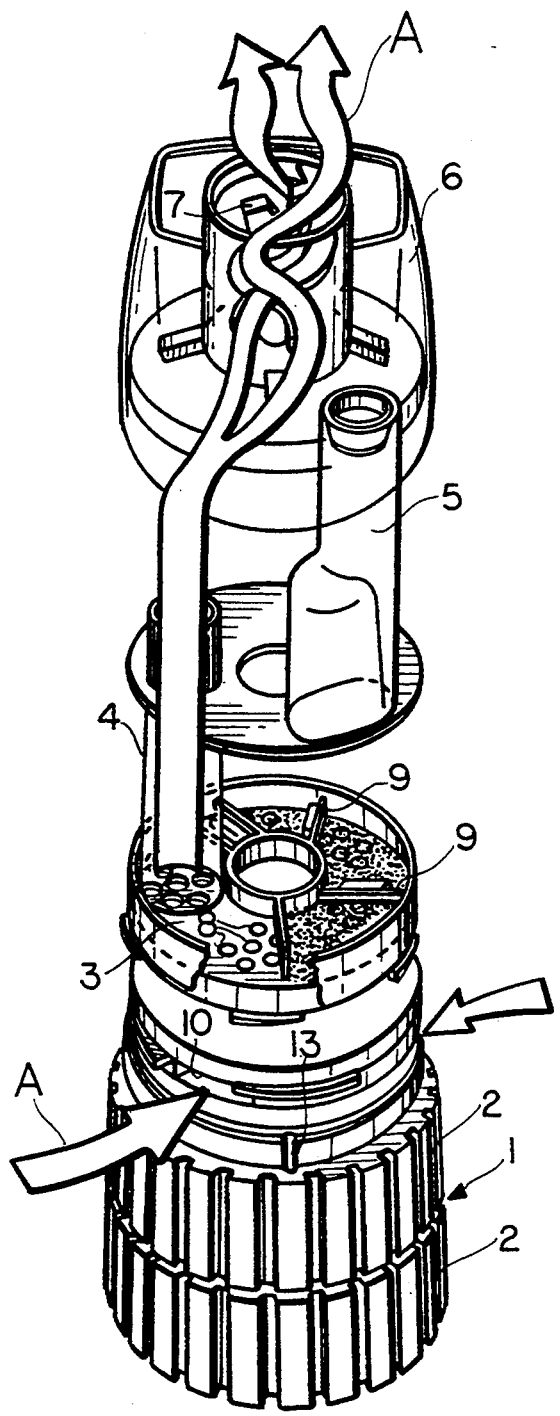

In FIG. 1 an exploded view of a powder inhaler is shown, which is driven by the patient's own breath. The airflow through the inhaler at the inhalation is marked by arrows A.

Figure 2:
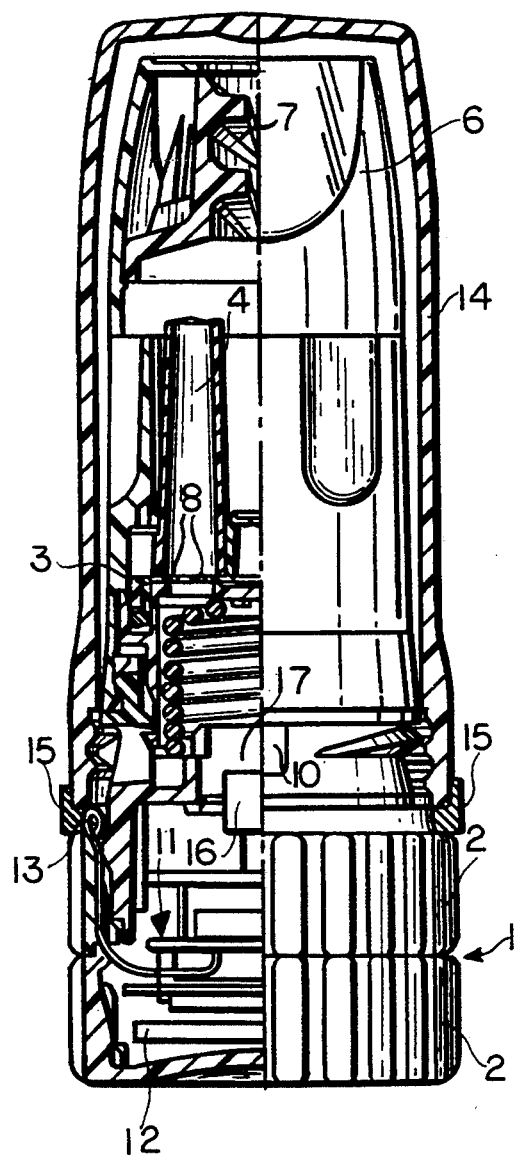

FIGS. 1 and 2 show the different parts of the powder inhaler. A pivotable control unit 1 with double grip rings 2 cooperates with a dosage unit 3, which, when the operating unit 1 is turned, feeds a powder dose to an inhalation channel 4. The active substance is kept in a substance container 5. A mouthpiece 6 is provided with an insert with narrow helical deflection devices 7 for decomposition of the substance powder into an inhalatable powder fraction. The dosage unit 3 is shaped as a flat, rotatable disc with groups of dosage holes 8 and the disc is arranged at the bottom of the substance container 5. The dosage holes 8 are filled with substance in the position below the substance container 5. When the grip rings 2 are turned and fed one step forward the dosage disc 3 is brought therewith in the rotation. A number of scrapers 9 are arranged to abut the dosage disc 3, whereby the scrapers remove excess powder substance above the dosage holes 8 at the turning of the dosage disc 3.

When the patient inhales from the mouthpiece opening, air flows through two opposite air inlets 10 in the operating unit 1 and through the group of dosage holes 8, which at the moment are exposed at the inhalation channel 4 situated above the dosage disc 3, further through the channel 4 and out through the mouthpiece 6. When the airflow passes the dosage holes 8 the dose of active substance loaded in the holes will be released and will be brought further on together with the air flow and will be decomposed in the helical passage in the mouthpiece 6.

Inside the two separable grip rings 2 of the operating unit an electronical unit 11 with a battery 12 as the source of voltage is arranged. Two contact surfaces 13 are arranged on the upper and outer side of the upper grip ring 2. When the inhaler is not used, a protective cover 14 is put over the mouthpiece 6 of the inhaler and down over the air intakes 10, whereby the protective cover 14 with its lower edge abuts the upper side of the upper grip ring 2. The lower edge of the protective cover 14 is provided with a metal contact ring 15. The contact ring 15 abuts the two contact surfaces 13 on the grip ring 2 when the protective cover 14 is put on, whereby the two contact surfaces 13 get electrical contact. A microphone 16 is arranged in direct connection with an air channel 17 between the air intakes 10 and the dosage disc 3 and the microphone is connected to the electronical unit 11 inside the operating unit 1. The microphone 16 can alternatively be placed in connection with the air channel, but separated from this through a thin diaphragm.

Figure 3A:
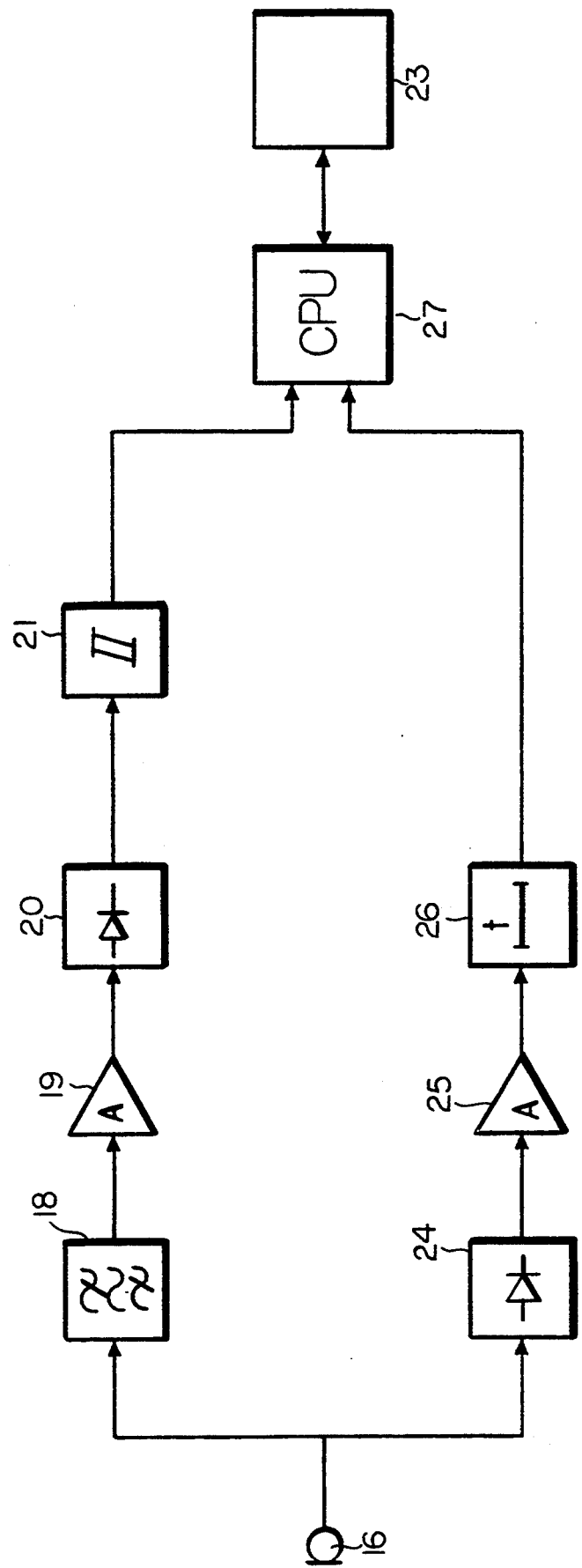

The electronical unit is explained more in detail with reference to the block diagram in FIG. 3a. The microphone 16 detects the sound of the "click", which occurs upon turning forward of a new dose and the sound of the airflow at an inhalation, and transfers these signals. A band pass filter 18 separates one for the inhalation typical and suitable working frequency (see FIG. 5). An amplifier 19 lifts up the signal level from the microphone 16, which leaves signals of the order of a few millivolts and the signals will here be amplified to about 1 V. The signal is rectified and is low pass filtered in a detector 20 so that the envelope of the signal is obtained. The envelope signal is a measure of the momentary air flow. A Schmitt trigger 21 quantitizes the signal and leaves the values "approved" and "not approved", respectively. The signal of the microphone is here transformed to a binary signal which states if the strength of the inhalation is sufficient. The hysteres of the Schmitt trigger makes that small variations in flow will not make the signal flutter between "approved" and "not approved".

Figure 3B:
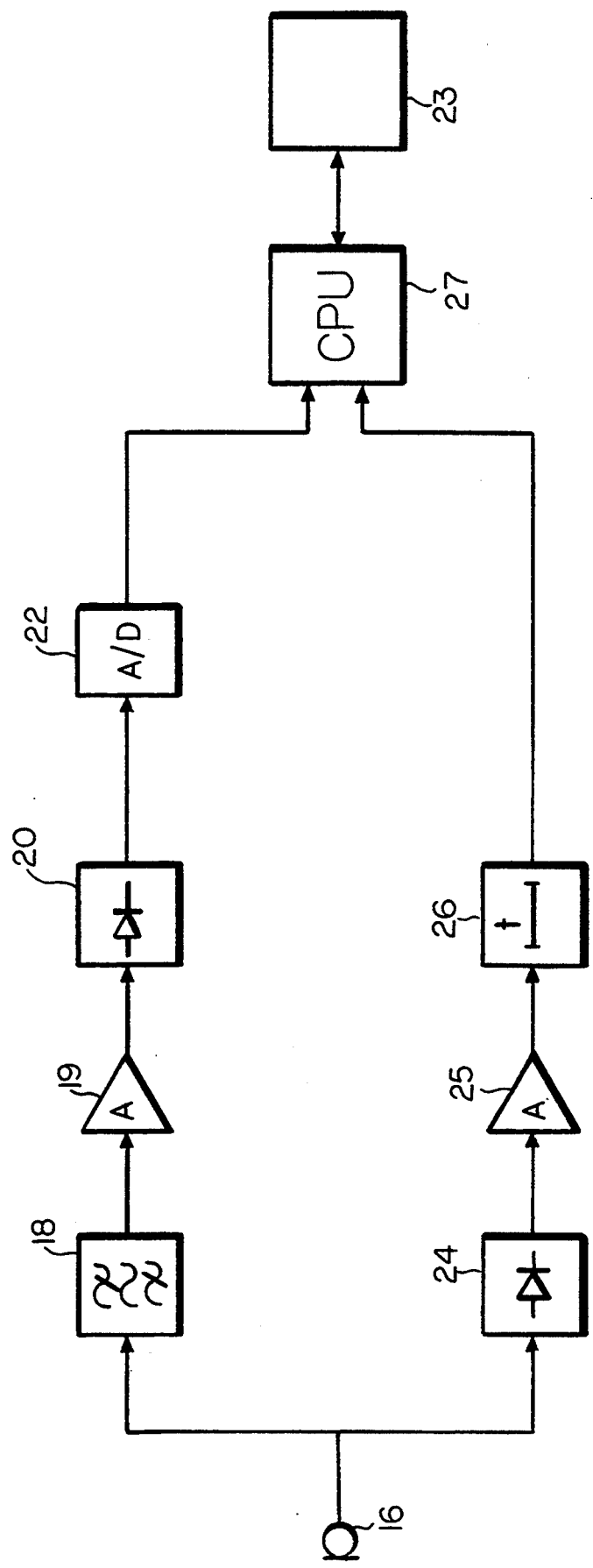

With the need of more than two quantitizing leves (approved/not approved) the Schmitt trigger 21 might be replaced by an analogue-digital-converter (A/D converter) 22, which is shown in FIG. 3b, the function of which is to measure the airflow one or several times during the inhalation. These results are stored together with a time notation in a memory 23 for further treatment.

The microphone signal, which is generated by the sound of the forward turning, is rectified in a detector 24 so that the absolute value of the signal is obtained. An amplifier 25 lifts the level of the signal from the microphone 16 to an order of about 1 V. This signal passes a puls stretcher 26, which stretches the short, transient "click" sound to a signal with logical levels and a sufficient duration for a processor to record it.

The processor 27 shall keep track of actual time, i.e. be a clock, collect the treated signals from the microphone and through these signals check that the patient takes his dosage in the prescribed way. The prescribed way means that the patient shall turn forward a dose and breath with a sufficient flow and sufficient duration in order to obtain an effective deposition in the lungs. The processor 27 performs the measurement of the length of the inhalation and transfers the time for an approved inhalation to the memory unit 23. The processor 27 also detects if the contact surfaces are short circuited, that is if the protective cover 14 is put on, and takes care of the communication with a reading unit, which reads the gathered information in the memory unit 23. The processor 27 supplies the band pass filter 18, the amplifier 19, the detector 20 and the Schmitt trigger 21 with power only when the protective cover 14 is not put on in order to save the battery 12 in this way.

The memory unit 23 is suitably comprised of an EPROM (Electrically Eraseably Programmable Read Only Memory), which is an electrically eraseable, fixed memory. An EPROM is preferably used here since the information must not be lost if the battery should be finished. In this memory the times of inhalation is saved for approved inhalations and optional inhalation measurement test results.

Figure 4:
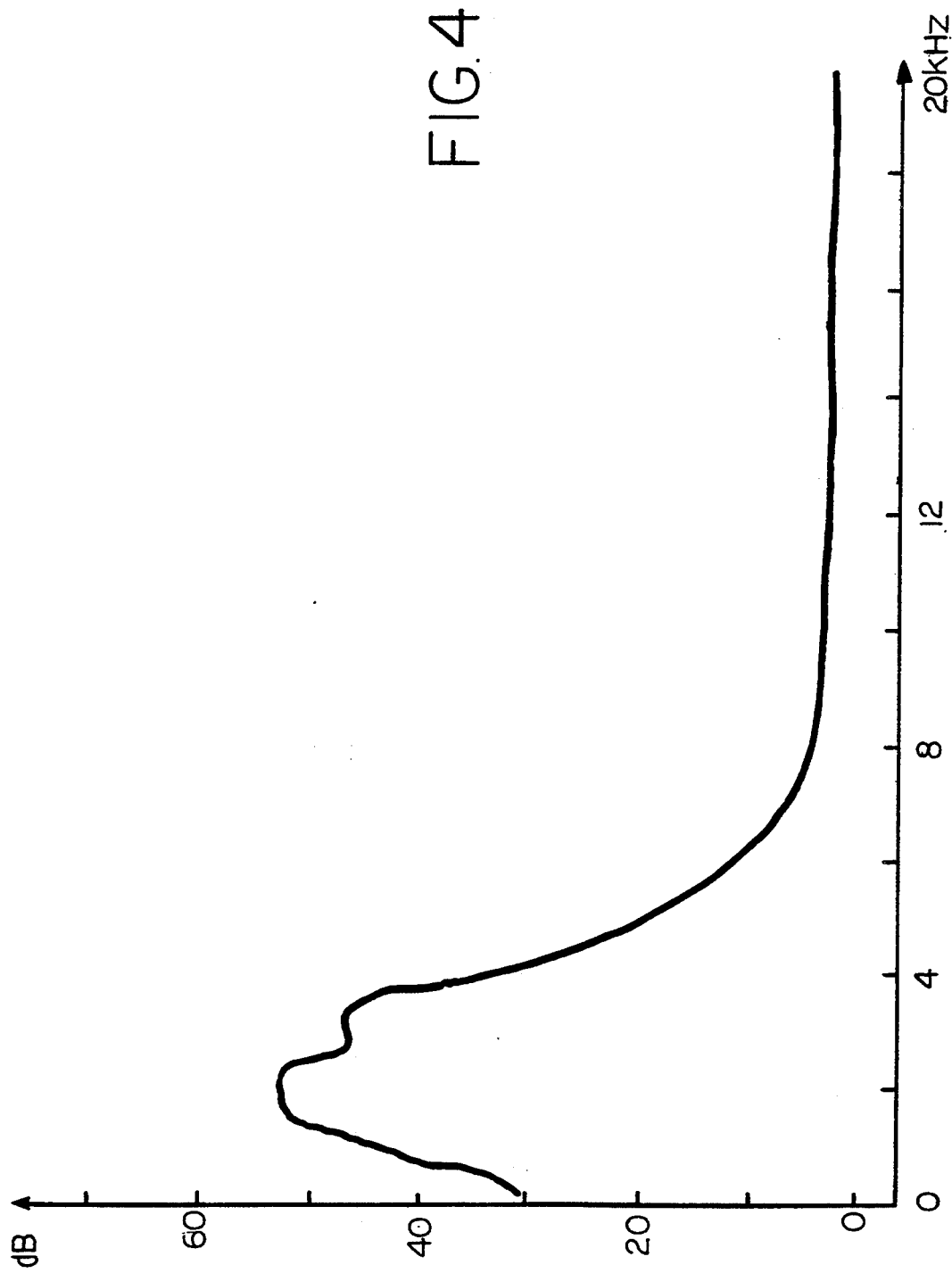

FIG. 4 shows a diagram of how disturbing noise from the outside, in this case music from the radio at an extremely high sound level, is captured by the microphone 16 inside the powder inhaler according to FIG. 2.

Figure 5:
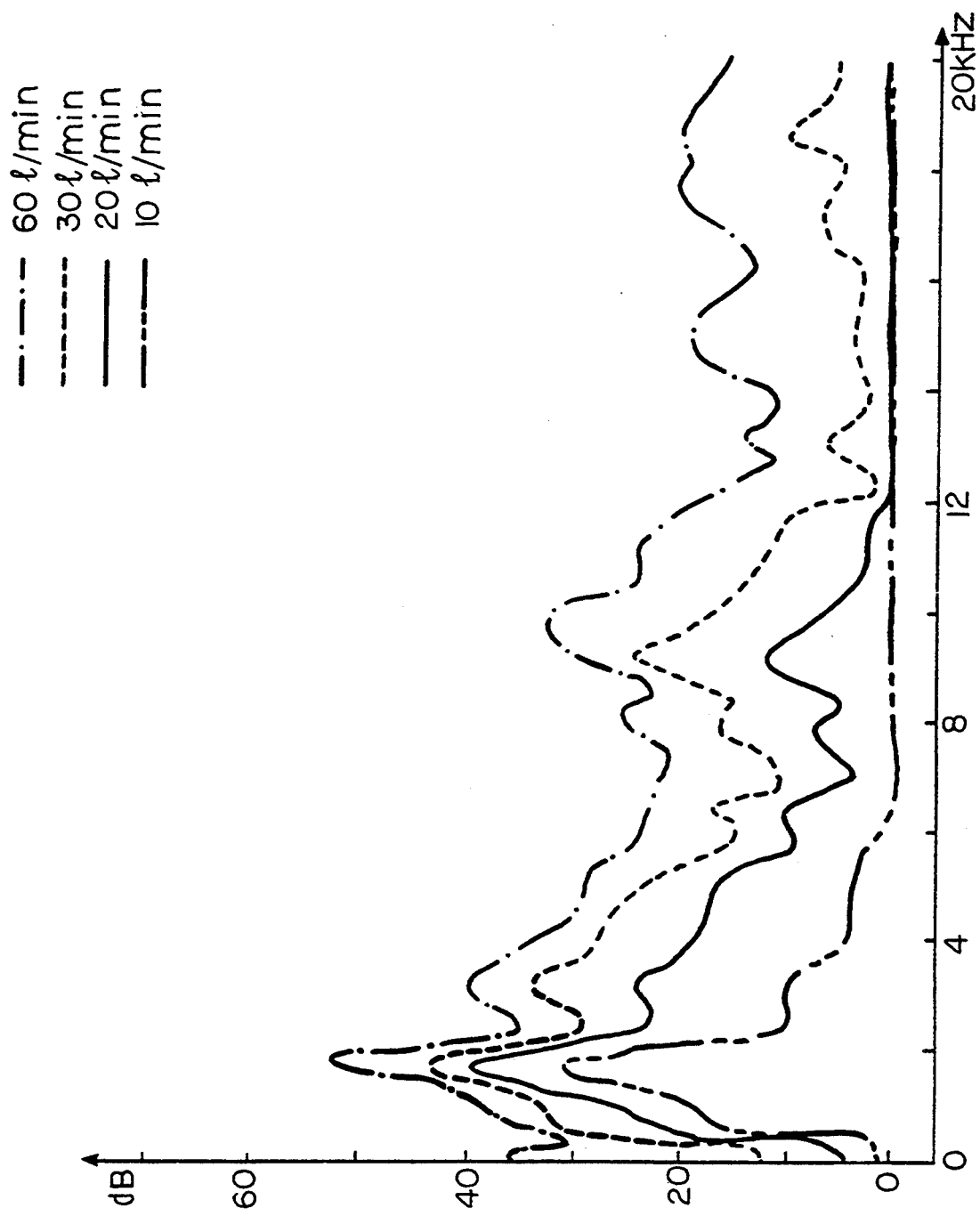

FIG. 5 shows the corresponding diagram of how the microphone 16 reacts to the airflow through the inhaler at the inhalation. The lower graph shows a sound spectrum for an airflow of 10 l/min, and the other graphs, in the upward direction, show the corresponding sound spectra for 20 l/min, 30 l/min and 60 l/min, respectively. The measuring range which is of interest for the air-flow lies in the range of between 20 l/min and 100 l/min. Since the measurements should be insensitive for outside noise disturbances it is evident from the graphs in FIGS. 4 and 5 that a signal at the frequency of 9 kHz is a suitable measuring signal in this embodiment.

Figure 6:
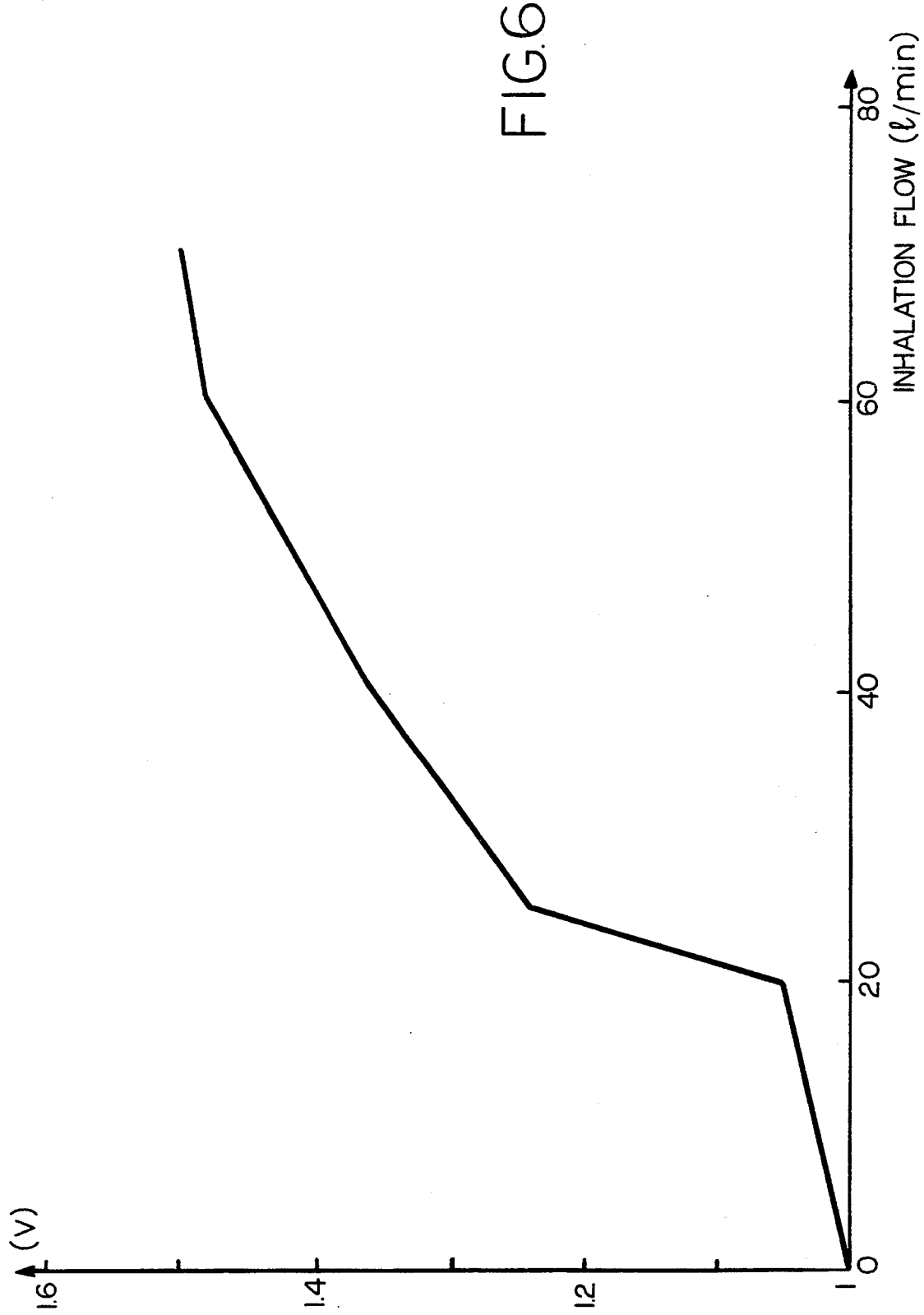

FIG. 6 shows the size of the measuring signal in Volts after filter and amplifier at inhalation flows from 20 l/min to 80 l/min.

When the patient shall medicate with the aid of the described powder inhaler, first he takes off the protective cover 14, whereby the contact ring 15 at the lower edge of the cover breaks the contact with the two contact surfaces 13 in the upper side of the upper grip ring 2, whereby the voltage to the band pass filter 18, the amplifier 19, the detector 20 and the Schmitt trigger 21 are connected. A dosage of active substance is fed forward to the inhalation channel 4 by turning the grip ring 2 forward one step. This turning forward creates a "clicking" sound which is detected by the microphone 16. When the turning forward is recorded by the processor 27 in the electronical unit the microphone 16 "listens" for the noise arising when the patient inhales through the inhaler and thereby inhales the dosage fed forward. Since the noise has a characteristic segment, only noise at this frequency is amplified by the amplifier 19. The signal after the amplifier is quantitized in two steps, insufficient flow or sufficient flow. Alternatively the signal can be measured at several levels with optional grading. When an approved inhalation is detected, the time for the inhalation is stored in the memory 23 and in the alternative case also the "value" of the inhalation is stored.

At the next coming visit to the doctor, the doctor can, by separating the two grip rings 2, get access to the electronical unit and read the memory 23 using a special reading equipment, which is connected to the electronical unit. This reading equipment reads the approved inhalation times and transfers the information to a computer, which can process and present the material in a way suitable for the doctor. In the alternative with quantitizing in more than two levels the "value" of the inhalation is also read, which can be presented as a flow/time diagram or as an inhalation measure, e.g. peak inspiratory flow, PIF of total volume (VC).

Figure 7:
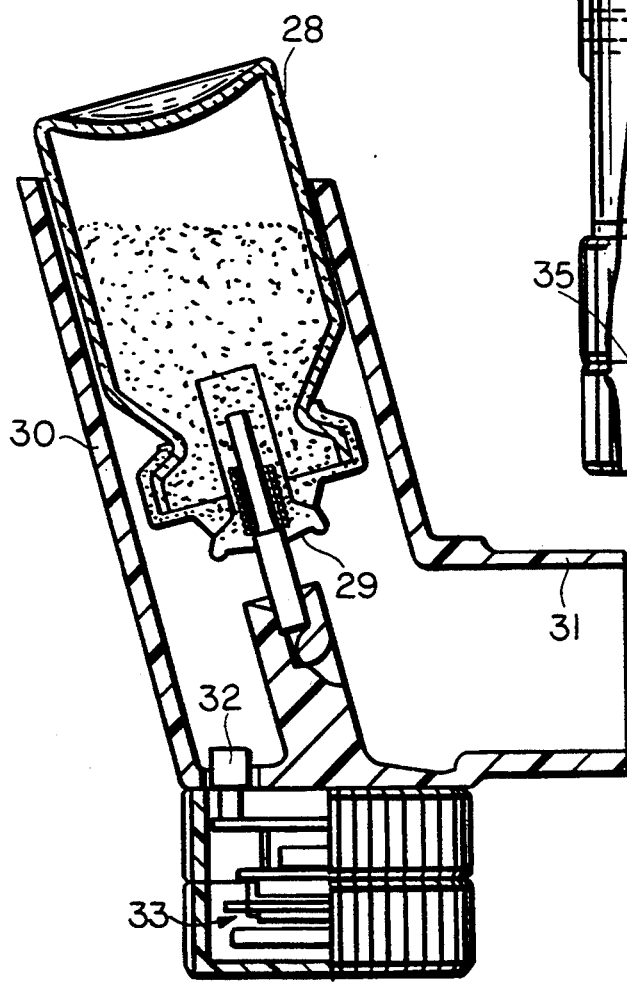

In FIG. 7 is shown a dose aerosol with pressure filled canister. The pressure canister 28 is provided with a nozzle 29 and is placed in a bracket 30 with a nozzle 31. The bracket 30 is shaped with a separable unit, which comprises a detector 32 in connection with the air channel for the inhalation flow and an electronical unit 33. When the patient inhales from the mouthpiece opening air flows past the gap around the pressure canister 28 and out through the mouthpiece 31.

In order to obtain perfect medication effect with a dose aerosol the patient shall, during the introductory phase of the inhalation, press the canister 28 down so that a dose is released through the nozzle 29. The air flow around the canister 28 and the bracket 30 give rise to a noise, which can be detected by a noise detector 32. When a dosage is released through the nozzle a sound arises, which can be distinguished from the noise and can be detected by the detector. Since these sounds are different from each other, a microphone can be used as detector also in this embodiment.

At inhalation through the inhaler according to FIG. 7 a pressure drop is created between the ambient pressure and the pressure at the mouthpiece opening, i.e. a sub-pressure arises inside the bracket 30 when the patient inhales, which sub-pressure can be detected by a pressure transmitter. At the release of a dose a strong pressure change with short duration arises, which is also detectable by a pressure transmitter. In the embodiment according to FIG. 7 thus also a pressure transmitter can be used for detection of both the inhalation and the release of a dose, i.e. the information necessary for controlling that the patient uses the dose aerosol in the prescribed way.

Figure 8:
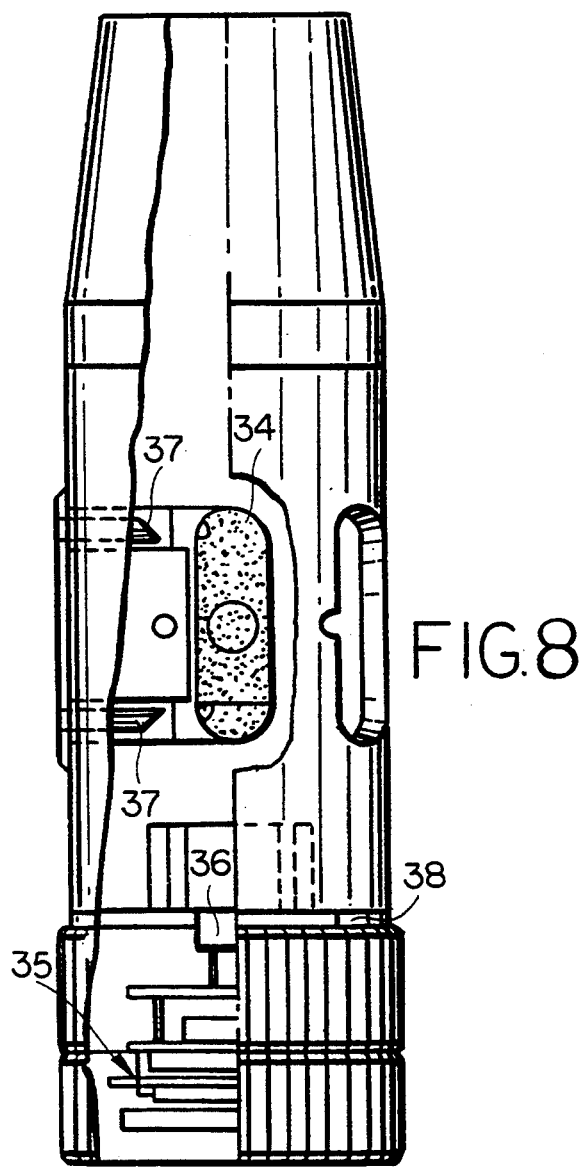

FIG. 8 shows a powder inhaler, which is loaded with a gelatine capsule 34 with powder substance. An electronical unit 35 with detector 36, preferably a microphone, works in a similar way as the powder inhaler shown in FIG. 2. When a capsule is placed in the inhaler it is punctuated/broken by needles 37 brought through the wall of the capsule. When the capsule has been punctuated/broken the substance will be available for the inhalation flow. The punctuation/braking of the capsule causes a short and intensive sound which is detected by the microphone 36. At inhalation here also arises a characteristic sound which is detected/measured in the same way as in the other embodiments.

Possible modifications of the invention

The device according to the invention is also suitable for use in an inhalator with rotating parts, e.g. of the type Rotacaps ® in that instead of measuring the level of the sound one measures the dominating frequency of the rotation sound. The recorded frequency images and can be transformed into a measure of the airflow through the inhaler.

In order to simplify the reading of the memory, any type of external computer contact might be arranged in the cover of the inhaler, thereby being accessible for reading without any need of demounting the inhaler.

We claim:

1. A portable inhaler device including medication storage means and including a passage through which inhalation air flows, said device having dispensing means for dispensing medication into said passage, said device comprising:

a single detector means disposed in said passage for detecting air flow as well as the availability of medication dispensed into said passage for inhalation and for generating electrical signals responsive thereto; and electronic means disposed in said device for recording the inhalation of medication responsive to predetermined values of said signals indicating adequate inhalation of medication in a prescribed manner to permit periodic determination of whether a prescribed dosage of medicine has been effected.

2. A device according to claim 1, wherein said dispensing means includes means for feeding of a medicine dose, and wherein said detector means comprises a sound detector for detecting the sound of feeding of a medicine dose as well as a sound arising at inhalation through said passage.

3. A device according to claim 2, wherein said sound detector comprises a microphone.

4. A device according to claim 2, comprising means including a schmitt trigger for converting signals from said sound detector to binary signals of approved and not approved inhalation, respectively.

5. A device according to claim 2, including an inhalation channel and comprising further a turnable dosage disc with dosage holes for dispensing powder, and means for rotating said disk step by step for moving successive doses to said inhalation channel, wherein said sound detector is arranged to detect sound produced by rotation of said dosage disc.

6. A device according to claim 5, including an air intake, and an air channel between said air intake and the dosage disc, wherein the sound detector is arranged close to said air channel for detecting the noise arising in the air channel at the inhalation.

7. A device according to claim 1, comprising an aerosol dispensing means, wherein the detector means comprises a pressure transmitter means for detecting a subpressure in said passage during inhalation as well as a momentary pressure change arising at the release of an aerosol dose.

8. A device according to claim 1, wherein said electronic means includes microprocessor means for receiving signals from said detector means, and readable memory unit means for storing signals from said microprocessor means.

9. A device according to claim 8, comprising a battery arranged to provide said electronic means with power, a removable protective cover having a metal ring, a pair of contacts which are positioned to be short circuited by the metal ring when the cover is in place, and circuit means for disconnecting power to said electronic means when said contacts are short circuited.

10. A method of dispensing medication; said method comprising the steps of; providing a portable inhaler device having dispensing means for making medication available for inhalation and a passage through which inhalation air flows, comprising the steps of providing a single detector within said passage:
   detecting within said detector the availability of a medicine dose and generating a first electrical signal responsive thereto;
   detecting with said detector the inhalation flow through the passage and generating a second electrical signal responsive thereto;
   providing said first and second electronic signals to a processor contained in said device;
   determining, responsive to said first and second electronic signals, if and how the performed medication shall be recorded; and
   recording the inhalation in a storage means contained in said device responsive to predetermined values of said signals.

11. A method according to claim 10, further comprising the step wherein the processor determines, responsive to the detected signals, whether the medication takes place in an approved way, and the step of recording the time of an approved medication in a memory unit.

* * * * *